(12) United States Patent
Zhao

(10) Patent No.: US 7,309,502 B2
(45) Date of Patent: Dec. 18, 2007

(54) PHARMACEUTICAL COMPOSITIONS FOR TREATING AND SAVING AND THE METHOD FOR THE PREPARATION THEREOF

(76) Inventor: Chaoying Zhao, Changhai Road 170-7-602, Shanghai (CN) 200003

( * ) Notice: Subject to any disclaimer, the term of this patent is extended or adjusted under 35 U.S.C. 154(b) by 84 days.

(21) Appl. No.: 11/198,696

(22) Filed: Aug. 5, 2005

(65) Prior Publication Data

US 2005/0288235 A1 Dec. 29, 2005

Related U.S. Application Data

(62) Division of application No. 09/713,498, filed on Nov. 15, 2000, now Pat. No. 6,986,905.

(51) Int. Cl.
| | |
|---|---|
| A61K 33/14 | (2006.01) |
| A61K 31/715 | (2006.01) |
| A61K 31/718 | (2006.01) |
| A61K 31/721 | (2006.01) |
| A61K 47/36 | (2006.01) |
| A61K 47/42 | (2006.01) |
| A61K 9/08 | (2006.01) |
| A61P 7/08 | (2006.01) |

(52) U.S. Cl. ............... 424/680; 424/678; 424/679; 424/697; 424/717; 514/2; 514/23; 514/54; 514/59; 514/460; 514/557; 514/669; 514/774; 514/823; 514/833; 514/921

(58) Field of Classification Search ............ None
See application file for complete search history.

(56) References Cited

OTHER PUBLICATIONS

Dubick, M.A. et al., "Issues of concern regarding the use of hypertonic/hyperoncotic fluid resuscitation of hemorrhagic hypotension," Shock, vol. 25, No. 4, pp. 321-328 (2006).*
Sheikh, A.A. et al., "Cerebral effects of resuscitation with hypertonic saline and a new low-sodium hypertonic fluid in hemorrhagic shock and head injury," Critical Care Medicine, vol. 24, No. 7, pp. 1226-1232 (1996).*
Velasco, R.T. et al., "Experimental basis for small-volume resuscitation: Physiologic mechanism for the circulatory effects provoked by hyperosmolar sodium chloride," Clencia e Cultura Journal of the Brazilian Association for the Advancement of Science, vol. 52(6), Dec. 2000, pp. 372-376.*

* cited by examiner

*Primary Examiner*—John Pak
(74) *Attorney, Agent, or Firm*—Mayback & Hoffman, P.A.; Gregory L. Mayback; Scott D. Smiley

(57) ABSTRACT

The present invention relates to a pharmaceutical composition and the method for the preparation thereof. The composition comprises 1.5~6.9% (w/v) of one or more substances selected from sodium chloride, sodium bicarbonate, potassium chloride, magnesium sulfate, calcium chloride, calcium gluconate, and the like, and 3~18% (w/v) of one or more substances selected from hydroxyethylstarch, dextran, carboxymethylstarch, polyvinyl-pyrrolidone, gelatin derivatives, and the like as well as the remainder of conventional injections, as long as sodium chloride is not less than 1.5% (w/v). The pharmaceutical composition of the present invention is used to treat and save the wounded and patients, as well as to treat shock, its advantages include safe and convention use, rapid and good curative effect, long time maintenance, extensive uses and the like.

10 Claims, No Drawings

PHARMACEUTICAL COMPOSITIONS FOR TREATING AND SAVING AND THE METHOD FOR THE PREPARATION THEREOF

CROSS-REFERENCE TO RELATED APPLICATIONS

This application is a divisional application of application Ser. No. 09/713,498, filed Nov. 15, 2000 now U.S. Pat. No. 6,986,905.

BACKGROUND OF THE INVENTION

Field of the Invention

The present invention relates to a novel pharmaceutical composition for treating and saving the wounded, and to a method for the preparation thereof.

Nowadays blood transfusion and fluid infusion are the important measures to treat and save the wounded, especially the traumatic shock. Usually, the principle of transfusion is "to infuse component the patient is deficient in, to supply how much the patient needs". For example, when the patient mainly lost his blood, he should be transfused with blood, even though sometimes the patient needs to be transfused with blood from normal individuals. When the patient mainly lost plasma, plasma or plasma volume expander should be transfused to him; when the patient mainly lost intercellular fluid, physiological saline should be infused. In fact, the treating and saving measures of formulating physiological solutions on the basis of normal composition of body, or transfusing with blood from normal individuals to the patient with evident physiopathological changes is to treat the organism as mechanical device, therefore these measures often have following disadvantages:

(1) Blood transfusion: In general, the volume of blood transfusion closes to or exceeds the volume of blood lost. If a big amount of blood is required, the blood source will be difficult, the cost is expensive. The preparation and storage need certain conditions. In addition, before transfusion, some time should be taken for blood typing and cross match tests, and only the substitutes could be used for the individuals with rare blood types. Blood transfusion could result in production of anti-platelet antibodies and anti-leucocyte antibodies, as well as various hematogenic infectious diseases, for example, AIDS, hepatitis B, hepatitis C. etc.

(2) Albumin infusion: There is a great demand, a great expense difficult source, complicated preparation method and certain requirements for, the method storage. After albumin infusion, it could effuse through capillaries, and couldn't be reabsorbed into vessel. Therefore interstitial edema will occur, and might result in pulmonary edema, renal failure, and cardiac insufficiency, by contrast enhance the mortality. Albumin infusion could result in evident decrease of $\alpha_1$, $\alpha_2$, $\beta$, $\gamma$-globulins and fibrinogen, cause reduction of immunity, and affect function of blood coagulation.

(3) Infusion of fluorocarbon as plasma substitute: It requires a large amount of the substitute and simultaneous inhalation of oxygen with high component pressure. Otherwise the demand of the organism is not met. The fluorocarbon as plasma substitute should be preserved in low temperature, and its transport is not convenient. For example, thirty minutes before infusion the patient should be injected with 10 mg of dexamethasone. The frozen injection for infusion should be thawed. Thus, the procedures are complicated. After infusion, the observation should be continued for 5-10 min. The infusion of fluorocarbon as plasma substitute could induce adverse reactions, such as anaphylaxis, hypotension, thrombocytopenia, hepatosplenomegaly, reduction of immunity, and abnormality of fibrinolysis system.

(4) Infusion of balanced buffers, its amount infused should be three times more than the volume of blood lost to maintain the blood pressure. 60-80% the solution infused could effuse out of the blood vessel, which results in tissue edema (for example, cerebral edema, pulmonary edema) and renal insufficiency, it could cause the difficulty for sequential therapy.

(5) Infusion of physiological saline. Its amount infused should also be three times more than the volume of blood lost. Its efficacy is poorer than balanced buffers, and its adverse effects are more significant.

To solve the problems in blood transfusion and infusion, the skilled in the art had studied anti-shock therapy with hypertonic sodium chloride solution. For example, 7.5% (w/v) NaCl solution suggested by Velasco. But the hypertonic NaCl solution has some toxicity to the organism.

Most investigators have proposed intravenous injection of hypertonic NaCl solution for anti-shock therapy, but it usually leads to obvious complications, such as hypotension, rupture of blood cells induced by extra hypertonic solution, cardiac insufficiency, decreased renal function and disorders of nervous system.

Thus, it can be showed that there is a demand for novel anti-shock drugs to reverse the physiopathological condition of shock, in order to obtain time for sequential therapy after the emergency treatment, and to create opportunity with improved effect of treating and saving the wounded and patients, and with increased survival rate.

SUMMARY OF THE INVENTION

An object of the present invention is to provide a pharmaceutical composition with convenient source, less dosage, rapid and better efficacy, less side effects, wider uses, and without restriction by blood type as well as without special storage condition.

Another object of the present invention is to provide the method for the preparation of the said pharmaceutical composition.

The present invention proposes a new concept of liquid therapy for shock, based on three aspects of thinking. The first aspect in connection with the present unreasonable dosage regimen, following principle is adopted: "to infuse what component the patient needs, then to infuse how much the patient needs". Based on the physiopathological status of the patient with shock, there is a prior demand for the compound solution containing hypertonic sodium ion (or combination of various crystals, or combination of various crystals and various colloids, etc.) to preliminarily improve micro-circulation, tissue perfusion, and hemodynamics immediately. Then in the light of practical demand the isosmotic solution or proper hypoosmotic solution or whole blood or concentrated red blood cell suspension is administered, in order to permit the latter infused solution better action when the patient's condition has improved preliminarily by the earlier hypertonic solution, and to remit overdehydration of some cells caused possibly by the hypertonic solution infused earlier. The second aspect, in connection with the present unreasonable ratio of colloids and crystals in the transfusion for patient with shock prepared on basis of their normal physiological concentrations, in view of the fact that the property and volume-expanding ability of artificial colloids are different from albumin in blood, it is considered that the transfusion with suitable ratio of colloids and crystals, instead of human normal physiological proportion, should be administered on basis of the physiopathological status of patients. Thus medicine administration according to indications could reduce the dosage, increase the efficacy, and decrease the complications. The third aspect, in connection with a lot of inadequacy in the present anti-shock experimental studies (such as animal model, reasonable concentration and infusion rate of hyperosmotic solutions), a great number of experimental studies have been conducted, and met with success.

Based on the above three aspects of thinking form the theoretical researches and the clinical experiences, the particular embodiments of the present invention have been completed through the animal experiments and the clinical practice.

The present invention is achieved through the following embodiments. A pharmaceutical composition comprising 1.5-6.9% (w/v) of one or more substances selected from sodium chloride, sodium bicarbonate, potassium chloride, magnesium sulfate, calcium chloride, calcium glaciate, calcium lactate, sodium lactate, sodium acetate and Tris (Hydroxy methyl) amino methane; and 3-18% (w/v) of one or more substances selected form hydroxyethylstarch, dextrin, carboxymethylstarch, polyvinyl-pyrrolidone (PVP), gelatin derivatives, condensed glucose, glucose, fructose, lactose, glycerin, xylitol, sodium alginate, N-2-hydroxypropylacrylamide, ethylene epoxide-polypropylene glycol, pectin, mannitol, and pentahydroxyethylstarch (Pentastarch) as well as the remainder of conventional injections, as long as sodium chloride is not less than 1.5% (w/v), and the concentration of sodium ion is not more than that of in 6.9% (w/v) sodium chloride solution or equivalent.

The preferred composition of the present invention consisting of 4.2±0.2 g sodium chloride and 7.6±0.6 g hydroxyethylstarch per 100 ml.

In the composition, the said hydroxyethylstarch contains at least 10% hydroxyethylstarch with molecular weight of 25,000 to 45,000. The said dextran has molecular weight of 40,000 to 230,000, carboxymethylstarch has molecular weight of 30,000 to 80,000, PVP has molecular weight of 5,000 to 700,000, condensed glucose has molecular weight of 8,000 to 12,000; sodium alginate has molecular weight of 20,000 to 26,000; pectin has molecular weight of 20,000 to 40,000; pentahydroxyethylstarch is the product of DuPont Company (Pentastarch) with molecular weight of 264,000.

The said gelatin derivatives have molecular weight of 20,000 to 35,000, and are selected from urea-conjugated gelatin, modified liquid gelatin, oxidized polygelatin and degraded gelatin poly-peptide.

Conventional injections are selected from water for injection, physiological saline, balanced buffers, glucose solution, sodium lactate solution, sodium acetate solution, Tris solution, and glucose and sodium chloride solution.

The composition of the present invention is prepared as following procedure: dissolving 3-18 g of total amount of one or more substances selected from hydroxyethylstarch, dextran, carboxymethylstarch, PVP, gelatin derivatives, condensed glucose, glucose, fructose, lactose, glycerin, xylitol, sodium alginate, N-2-hydroxypropylacrylamide, ethylene epoxide-polypropylene glycol, pectin, mannitol, and pentahydroxyethylstarch in 100 ml of total volume of one injection or mixture of several injections selected from water for injection. physiological saline, balanced buffers, glucose solution, sodium lactate solution, sodium acetate solution, Tris solution, and glucose and sodium chloride solution; then adding 1.5 g sodium chloride and 0-5.4 g of one or more substances selected from sodium chloride, sodium bicarbonate, potassium chloride, magnesium sulfate, calcium chloride, calcium gluconate, calcium lactate, sodium lactate, sodium acetate, and Tris; with the proportion described above, then mixing, and dissolving, to obtain the composition of the present invention.

The preferred technical embodiments are as follows: (i) preparation of hydroxyethylstarch: According to the proportion of 1:0.8-0.875: 0.04-0.042 (w/v/v), corn starch or sorghum starch, and 95% ethanol, and 35-38% hydrochloric acid are mixed, the temperature is raised to 65-80 C for hydrolysis of starch, 16% sodium hydroxide solution is added in proportion of 0.6-0.7:1 (v/w) of stated solution versus starch. Then ethylene epoxide is added in proportion of 0.35-0.5:1 (w/w) of ethylene epoxide versus starch, then the mixture is heated to 65-75 C to cause starch hydroxyethylation. (ii) Formulation of the composition: Appropriate volume of water is added, to prepare 7.6±0.6% (w/v) hydroxyethylstarch solution. Suitable amount of activated charcoal is added to discolor the solution through adsorption. After filtration, the pH is adjusted to 5.5-7, and the total of 4.2±0.2 g of sodium chloride is added, suitable amount of activated charcoal is added again for adsorption and discolor action. After filtrated through 0.8 μm micro-porous filter, the preferred composition of the present invention is obtained.

The present invention is further illustrated in detail by the following examples.

PREPARATIVE EXAMPLE

Preparation of Hydroxyethylstarch.

100 g Corn or sorghum starch are mixed with 87 ml of 95% ethanol and 4.2 ml of 35% hydrochloric acid. The temperature is raised to 70 C to hydrolyze starch then 60 ml at 16% sodium hydroxide solution is added, then 45 g epoxyethane is added, and the mixture is heated to 70 C to complete hydroxyethylation of starch. According to the formula and preparative method described above hydroxyethylstarch with molecular weight of 25.000-45.000 is obtained.

Example 1

Prepare According to the Following Proportion:

| Hydroxyethylstarch | 7.6 g |
|---|---|
| sodium chloride | 4.2 g |
| water for in injection | added to 100 ml |

7.6 g hydroxyethylstarch are dissolved in 100 ml of water for injection. 0.5 g of activated charcoal is added, and the mixture is heated at 90 C for 15 min under stirring. After filtration through asbestos plate filter, 4.2 g sodium chloride (purity pharmaceuticals use) are added, and dissolved with stirring. 0.5 g activated charcoal is added, and the mixture is heated at 90 C for 10 min under stirring. After filtration through asbestos plate filter and 0.8 μm micro-porous filter. Resulted filtrate is transferred into 250 ml or 500-ml glass or plastic bottles (bags), after sealing the bottles or bags are 1.05 kg/cm$^2$ and 121-123 C for 15-30 min for sterilization, to obtain the pharmaceutical composition of the present invention.

Example 2

Prepare according to the following proportion:

| | |
|---|---|
| Dextran | 9 g |
| hydroxyethylstarch | 3 g |
| sodium chloride | 1.5 g |
| sodium bicarbonate | 3.4 g |
| physiological saline | added to 100 ml |

Above-mentioned dextran (produced by Shanghai Glucose Factory), hydroxyethylstarch (prepared according to preparative example) are dissolved in physiological saline, and adsorbed and discolored with activated charcoal according to the method stated in Example 1. Then above-mentioned sodium chloride, sodium bicarbonate, are added in turn, and dissolved with stirring. There after the obtained solution is discolored, filtered, sterilized and filled, to obtain the pharmaceutical composition of the present invention.

Example 3

Prepare according to the following proportion:

| | |
|---|---|
| polyvinyl-pyrrolidone (PVP) (produced by Bayer) | 12 g |
| sodium chloride | 2 g |
| sodium acetate | 4 g |
| 10% glucose solution | added to 100 ml |

According to the method described in Example 2 except that dextran and hydroxyethylstarch is replaced by PVP, sodium bicarbonate is replaced with sodium acetate, and physiological saline is replaced with glucose solution, the composition of the present invention is obtained.

Example 4

Prepare according to the following proportion:

| | |
|---|---|
| sodium alginate (produced by Nanning Pharmaceutical Factory, Guangxi) | 18 g |
| sodium chloride | 1.5 g |
| water for injection | added to 100 ml |

According to the method described in Example 1 to prepare the above-mentioned formulation, thus obtaining the pharmaceutical composition of the present invention.

Example 5

Prepare according to the following proportion:

| | |
|---|---|
| pectin (produced by PLA No. 185 Hospital) | 3 g |
| Pentahydroxyethylstarch (produced by DuPont Company) | 4 g |
| sodium chloride | 4 g |
| mannitol | 7 g |
| 2% sodium lactate solution | added to 100 ml |

According to the method in described in Example 1, pectin, Pentahydroethylstarch and mannitol are dissolved in sodium lactate solution, then sodium chloride is added and dissolved.

Example 6

Prepare according to the following proportion:

| | |
|---|---|
| condensed glucose (produced by southwest No. 5 Pharmaceutical Factory Chongqing) | 7 g |
| N-2-hydroxy propyl acrylamide | 2 g |
| sodium chloride | 4.4 g |
| water for injection | added to 100 ml |

Using the method in Example 1, the pharmaceutical composition of the present invention is prepared according to the above mentioned formula.

Example 7

Prepare according to the following proportion:

| | |
|---|---|
| fructose (produced by Shanghai No. 2 Reagent Factory) | 5 g |
| xylitol (produced by Liaoyang organic Chemical Plant) | 4 g |
| sodium chloride | 4.8 g |
| water for injection | added to 100 ml |

Using the method in Example 1, the pharmaceutical composition of the present invention is prepared according to the above-mentioned formula.

Example 8

Prepare according to the following proportion:

| | |
|---|---|
| glycerin | 2 g |
| lactose (produced by Shanghai No. 2 chemistry Reagent Factory) | 5 g |
| sodium chloride | 6 g |
| water for injection | added to 100 ml |

Using the method in Example 1, the pharmaceutical composition of the present invention is prepared according to the above-mentioned formula.

Test 1: Animal Experiment

From adult healthy hybrid dogs, regardless of sex, under local anesthesia, isolate femoral artery and femoral vein, then insert catheters respectively.

The arterial duct is connected to CF-II model monitor of cardiovascular function [Shanghai approval document number: Hu-Yao-Qi-Jian (Zhun)-97-221103] to monitor cardiovascular status. Bleed these dogs to monitor cardiovascular status. Bleed these dogs to mean arterial pressure (MAP) of 40-50 mmHg for a period of about 15 min. Maintain this blood pressure level for 1 hour, then infuse the product prepared in Example 1 at the dose of 8 ml/kg.

Monitor the cardiovascular function and urine volume over 4 hours after infusion. In the following tables, the blood pressure and other indexes are expressed as percentage of their basal levels respectively, the unit of urine volume is ml/kg body weight/h.

TABLE 1

Comparison between the composition of the invention and whole blood in equal volume of recovery of Cardiovascular function in dogs with shock [unit: % compared with respective basal level]

| | | After transfusion | | | | |
| --- | --- | --- | --- | --- | --- | --- |
| | | 30 min | 1 h | 2 h | 3 h | 4 h |
| Systolic pressure | composition of the invention | 75 ± 4 | 76 ± 4 | 77 ± 4 | 78 ± 5 | 79 ± 5 |
| | equal volume of whole blood | 67 ± 5 ($p < 0.01$) | 69 ± 6 ($p < 0.01$) | 73 ± 4 ($p < 0.05$) | 73 ± 4 ($p < 0.05$) | 77 ± 7 |
| diastolic pressure | composition of the invention | 77 ± 5 | 79 ± 5 | 81 ± 4 | 81 ± 5 | 81 ± 5 |
| | equal volume of whole blood | 69 ± 6 ($p < 0.01$) | 73 ± 8 ($p < 0.05$) | 76 ± 7 ($p < 0.05$) | 76 ± 7 ($p < 0.05$) | 82 ± 12 |
| mean arterial pressure | composition of the invention | 76 ± 4 | 78 ± 4 | 79 ± 4 | 80 ± 5 | 80 ± 5 |
| | equal volume of whole blood | 68 ± 5 ($p < 0.01$) | 71 ± 6 ($p < 0.01$) | 74 ± 4 ($p < 0.05$) | 75 ± 4 ($p < 0.05$) | 80 ± 8 |
| cardiac contractility | composition of the invention | 77 ± 5 | 79 ± 5 | 81 ± 4 | 81 ± 4 | 81 ± 5 |
| | equal volume of whole blood | 69 ± 6 ($p < 0.01$) | 73 ± 8 ($p < 0.05$) | 76 ± 7 ($p < 0.05$) | 76 ± 8 ($p < 0.05$) | 82 ± 12 |
| cardiac output | composition of the invention | 105 ± 13 | 106 ± 14 | 103 ± 14 | 106 ± 12 | 106 ± 17 |
| | equal volume of whole blood | 89 ± 10 ($p < 0.05$) | 83 ± 18 ($p < 0.01$) | 83 ± 15 ($p < 0.01$) | 88 ± 23 ($p < 0.01$) | 88 ± 16 |
| end-diastolic volume | composition of the invention | 82 ± 4 | 82 ± 3 | 83 ± 4 | 84 ± 3 | 84 ± 4 |
| | equal volume of whole blood | 78 ± 7 ($p < 0.05$) | 78 ± 9 ($p < 0.05$) | 80 ± 7 | 82 ± 8 | 84 ± 8 |

TABLE 2

Comparison between composition of the invention and equal volume of whole blood For urine volume in restoration stage in shocked dogs [unit: ml/kg/h]

| | After transfusion | | | |
| --- | --- | --- | --- | --- |
| | 1 h | 2 h | 3 h | 4 h |
| Composition of the invention | 2.23 ± 1.03 | 0.94 ± 0.22 | 0.95 ± 0.29 | 1.00 ± 0.30 |
| equal volume of whole blood | 0.33 ± 0.21 ($p < 0.01$) | 0.27 ± 0.16 ($p < 0.01$) | 0.73 ± 0.41 | 0.61 ± 0.25 ($p < 0.05$) |

Test 2. Human Body Clinical Experiment

The composition of the Example 1 of the invention was administered to 48 patients in Hefei No. 105 Hospital, Anhui province. The total effective rate was 100%. Most patients, had the blood pressure raised, urine volume increased, and the limbs became warm during transfusion. Several patients whom the conventional drugs couldn't already reverse, the composition of the Example 1 of the invention begin to play its role 5 to 10 minutes after infusion. The circulatory function of patients has recovered basically, (and there were no obvious clinical complications.

Test 3. Experiment of Acute Toxicity

When dogs were given at 2.5 times the dosage for human, no adverse effects have been showed. At 5 times the recommended dosage, salivation and vomiting were seen in the dogs. At 3.75 times the recommended dosage vomiting was seen without salivation in the dogs. All the above administered dogs survived more than 45 days. At 7.5 times the recommended dosage the death occurred in the administered dogs. Focal hemorrhage was seen in the lungs as target organs.

The composition of the present invention could be infused through vein at the dose of 8 ml of the composition of the present invention per kg body weight. It could be used directly in treating and saving the patients with shock, combined injuries or hematorrhea etc in order, to reverse the physio-pathological status of patients and to obtain time for sequential treatment.

As compared with the prior art, the pharmaceutical composition of this invention has the following prominent features and improvement:

1. Greatly decreased volume of transfusion: In general, the dose for most patients is 500 ml or less than 500 ml. Even if the patients suffered from lethal hematorrhea, to infuse only ¼ to ⅙ of volume of lost blood is enough. Thus, it could obviously decrease the incidence rate of tissue edema or overload of heart.

2. Rapid curative effect just during 5-10 minutes after infusion, the hemodynamics has been improved significantly.

3. Good efficacy. As Test 1 showed the composition of the invention had better efficacy than that of equal volume of fresh whole blood. Moreover, although the composition of the invention has no oxygen-carrying action, but it could improve micro-circulation and general status to decrease oxygen consumption and to increase oxygen transport. Thus at least 50% of blood transfused could be saved, it could mitigate the contradiction with short supply of blood, decrease the complications induced by blood transfusion, and reduce obviously the economic burden for the patients.

4. Maintain once of efficacy for long time. As Test 1 showed, after infusion of the composition of the invention, the improvement of hemodynamics and general condition could be maintained more than 3-4 hours, even if all other infusion and drugs were not administered.

5. Unnecessary special condition for storage: The composition could be stored at room temperature, simply used infused intravenously or intraosseously and conveniently transported, without special devices and special vehicles.

6. Unnecessary blood typing and cross match tests: It is suitable for individual with any blood type. Thus the valuable time could be gained to rescue the wounded and patients.

7. Wider uses: It could widely be used in the treatment of patients with shock of various types, brain trauma, burn, combined injuries, cardiogenic shock induced by myocardial infarction of right ventricle, hypotension induced by hemodialysis, biliary pancreatitis, cardiovascular intoxication induced by narcotic, hepatic echinococcosis, and patients under operation.

8. Change of administration model: The composition of the invention could be infused drop by drop intravenously, instead of pushing so it could be conveniently used with less complications.

In general, as compared with prior therapy, the composition of the present invention possesses unique benefit and theoretical innovation, for treating and saving the wounded and patients, so it is active significance.

I claim:

1. A pharmaceutical composition consisting essentially of:
   a first substance comprising sodium chloride in an amount between about 1.5% and 6% (w/v);
   a second substance comprising a gelatin derivative having a molecular weight of about 20,000-35,000 atomic mass units and selected from the group consisting of urea-conjugated gelatin, modified liquid gelatin, oxidized polygelatin and degraded gelatin polypeptide, and mixtures thereof in an amount between about 3 and 18% total (w/v);
   a third substance comprising at least one of sodium bicarbonate, potassium chloride, magnesium sulfate, calcium chloride, calcium gluconate, calcium lactate, sodium lactate, and Tris (Hydroxymethyl) aminomethane in an amount that is greater than 0% and less than or equal to 5.4% total (w/v); and
   an injection comprising at least one of water, physiological saline, balanced buffers, glucose solution, sodium lactate solution, Tris solution, and glucose and sodium chloride solution in an amount between about 75.1% and 95.5% total (w/v),
      wherein the total sodium ion concentration does not exceed an equivalent sodium ion concentration of 6.9% (w/v) sodium chloride solution.

2. The pharmaceutical composition of claim 1, wherein:
   said first substance comprises sodium chloride in an amount between about 4.0 and about 4.4 g per 100 ml; and
   said second substance is said gelatin derivative in an amount between about 7.0 g and about 8.2 g per 100 ml.

3. A method for preparing the pharmaceutical composition of claim 1, comprising:
   dissolving an amount between about 3 g and 18 g of said second substance in a total of 100 ml of said injection;
   adding 1.5 g of said first substance;
   adding said third substance; and
   mixing said injection to dissolve said first, second and third substances therein.

4. A method for preparing the pharmaceutical composition of claim 1, comprising:
   dissolving an amount between about 3 g and 18 g of said second substance in a total of 100 ml of said injection;
   adding 1.5 g of said first substance;
   adding an amount that is greater than 0 and less than equal to about 5.4 g of said third substance, such that the total sodium ion concentration based on said first, second and third substances does not exceed an equivalent sodium ion concentration in a 6.9% (w/v) sodium chloride solution; and
   mixing said injection to dissolve said first, second, and third substances therein.

5. The pharmaceutical composition according to claim 1, wherein said first substance is present in an amount between approximately 1.5% and approximately 4.4% total (w/v).

6. The pharmaceutical composition according to claim 1, wherein said first substance is present in an amount between approximately 4.0% and approximately 4.4% total (w/v).

7. A pharmaceutical composition consisting essentially of:
   a first substance comprising sodium chloride in an amount between about 4.0 and about 4.4 g per 100 ml;
   a second substance comprising a gelatin derivative having a molecular weight of about 20,000-35,000 atomic mass units and selected from the group consisting of urea-conjugated gelatin, modified liquid gelatin, oxidized polygelatin and degraded gelatin polypeptide, and mixtures thereof in an amount between about 7.0 g and about 8.2 g per 100 ml;
   a third substance comprising at least one of sodium bicarbonate, potassium chloride, magnesium sulfate, calcium chloride, calcium gluconate, calcium lactate, sodium lactate, and Tris (Hydroxymethyl) aminomethane in an amount that is greater than 0% and less than or equal to 2.5% total (w/v); and
   an injection comprising at least one of water, physiological saline, balanced buffers, glucose solution, sodium lactate solution, Tris solution, and glucose and sodium chloride solution in an amount between about 84.9% and 89.0% total (w/v),
      wherein the total sodium ion concentration does not exceed an equivalent sodium ion concentration of 6.9% (w/v) sodium chloride solution.

8. A pharmaceutical composition consisting essentially of:
   a first substance comprising sodium chloride in an amount of about 1.5 g;
   a second substance comprising:
      a gelatin derivative having a molecular weight of about 20,000-35,000 atomic mass units and selected from the group consisting of urea-conjugated gelatin, modified liquid gelatin, oxidized polygelatin and degraded gelatin polypeptide, and mixtures thereof in an amount of about 3 g; and
      dextran in an amount of about 9 g;
   a third substance comprising sodium bicarbonate in an amount of about 3.4 g; and
   an injection comprising physiological saline in an amount of about 83.1% total (w/v),
      wherein the total sodium ion concentration does not exceed an equivalent sodium ion concentration of 6.9% (w/v) sodium chloride solution and the total volume of the composition is 100 ml.

9. A pharmaceutical composition consisting essentially of:
   a first substance comprising sodium chloride in an amount of about 4.2 g;
   a second substance comprising a gelatin derivative having a molecular weight of about 20,000-35,000 atomic mass units and selected from the group consisting of urea-conjugated gelatin, modified liquid gelatin, oxidized polygelatin and degraded gelatin polypeptide, and mixtures thereof in an amount of about 7.6 g;
   a third substance comprising at least one of sodium bicarbonate, potassium chloride, magnesium sulfate, calcium chloride, calcium gluconate, calcium lactate, sodium lactate, and Tris (Hydroxymethyl) aminomethane in an amount that is greater than 0% and less than or equal to 2.7% total (w/v); and
   an injection comprising water in an amount between about 85.5% and 88.2% total (w/v),
      wherein the total sodium ion concentration does not exceed an equivalent sodium ion concentration of 6.9% (w/v) sodium chloride solution.

10. A pharmaceutical composition consisting of:
a first substance comprising sodium chloride in an amount between about 1.5% and 6% (w/v);
a second substance comprising a gelatin derivative having a molecular weight of about 20,000-35,000 atomic mass units and selected from the group consisting of urea-conjugated gelatin, modified liquid gelatin, oxidized polygelatin and degraded gelatin polypeptide, and mixtures thereof in an amount between about 3 and 12% total (w/v);
a third substance comprising at least one of sodium bicarbonate, potassium chloride, magnesium sulfate, calcium chloride, calcium gluconate, calcium lactate, sodium lactate, and Tris (Hydroxymethyl) aminomethane in an amount that is greater than 0% and less than or equal to 5.4% total (w/v); and
an injection comprising at least one of water, physiological saline, balanced buffers, glucose solution, sodium lactate solution, Tris solution, and glucose and sodium chloride solution in an amount between about 75.1% and 95.5% total (w/v),
wherein the total sodium ion concentration does not exceed an equivalent sodium ion concentration of 6.9% (w/v) sodium chloride solution.

* * * * *